US007012101B2

(12) United States Patent
Seyler et al.

(10) Patent No.: US 7,012,101 B2
(45) Date of Patent: *Mar. 14, 2006

(54) ARTIFICIAL TANNING EMULSIONS COMPRISING SORGHUM EXTRACTS/ORGANOMODIFIED SILICONES

(75) Inventors: Nathalie Seyler, Maisons-Alfort (FR); Iréne Elguidj, Neuilly (FR); Didier Candau, Bievres (FR)

(73) Assignee: L'Oreal, Paris (FR)

( * ) Notice: Subject to any disclaimer, the term of this patent is extended or adjusted under 35 U.S.C. 154(b) by 336 days.

This patent is subject to a terminal disclaimer.

(21) Appl. No.: 10/338,713

(22) Filed: Jan. 9, 2003

(65) Prior Publication Data

US 2003/0181533 A1 Sep. 25, 2003

Related U.S. Application Data

(60) Provisional application No. 60/350,383, filed on Jan. 24, 2002.

(30) Foreign Application Priority Data

Jan. 10, 2002 (FR) .................................. 02 00254

(51) Int. Cl.
  *B01F 17/00* (2006.01)
  *B01F 3/08* (2006.01)
  *A61K 7/00* (2006.01)

(52) U.S. Cl. ............................ 516/53; 424/59; 424/60; 424/400; 424/401

(58) Field of Classification Search .................. 516/53
See application file for complete search history.

(56) References Cited

U.S. PATENT DOCUMENTS

| 6,241,785 | B1 | | 6/2001 | Darmenton et al. | |
|---|---|---|---|---|---|
| 6,471,949 | B1 | * | 10/2002 | Candau et al. | 424/59 |
| 6,511,656 | B1 | * | 1/2003 | Candau et al. | 424/59 |
| 6,537,528 | B1 | * | 3/2003 | Candau et al. | 424/59 |
| 6,558,655 | B1 | * | 5/2003 | Candau et al. | 424/59 |
| 6,699,462 | B1 | * | 3/2004 | Seyler et al. | 424/59 |
| 6,875,426 | B1 | * | 4/2005 | Candau | 424/59 |
| 2002/0161104 | A1 | | 10/2002 | Labroussse et al. | |

FOREIGN PATENT DOCUMENTS

| EP | 1172091 A1 * | 1/2002 |
|---|---|---|
| EP | 1172092 A1 * | 1/2002 |
| EP | 1172093 A1 * | 1/2002 |
| EP | 1 230 914 A1 | 8/2002 |
| FR | 2 757 383 A1 | 6/1998 |
| FR | 2811555 A1 * | 1/2002 |

OTHER PUBLICATIONS

French Search Report Issued on Sep. 24, 2002 Corresponding to FR 02/00254, 3 Pages.

* cited by examiner

*Primary Examiner*—Randy Gulakowski
*Assistant Examiner*—Timothy J. Kugel
(74) *Attorney, Agent, or Firm*—Buchanan Ingersoll, P.C.

(57) ABSTRACT

Topically applicable, cosmetic/dermatological artificial tanning emulsions devoid of certain flavylium salts include (a) at least one aqueous phase and (b) at least one fatty phase, (c) an effective artificial tanning amount of at least one sorghum extract, and (d) at least one organomodified silicone.

32 Claims, No Drawings

US 7,012,101 B2

ARTIFICIAL TANNING EMULSIONS COMPRISING SORGHUM EXTRACTS/ORGANOMODIFIED SILICONES

CROSS-REFERENCE TO PRIORITY/PROVISIONAL APPLICATIONS

This application claims priority under 35 U.S.C. § 119 of FR-02/00254, filed Jan. 10, 2002, and of provisional application Ser. No. 60/350,383, filed Jan. 24, 2002, the latter being hereby expressly incorporated by reference.

CROSS-REFERENCE TO COMPANION APPLICATION

Application Ser. No. 10/338,700, filed concurrently herewith and assigned to the assignee hereof, now U.S. Pat. No. 6,699,462.

BACKGROUND OF THE INVENTION

1. Technical Field of the Invention

The subject of the present invention is a cosmetic or dermatological emulsion, characterized in that it comprises:
at least one aqueous phase and
at least one fatty phase;
at least one *sorghum* extract;
at least one organomodified silicone; the said composition not containing a flavylium salt which is unsubstituted in position 3 and which is substituted with at least one hydroxyl or alkoxy radical.

The invention also relates to its uses for the manufacture of cosmetic or dermatological compositions for coloring the skin.

2. Description of the Prior Art

Nowadays, it is important to look healthy and a tanned skin is always a sign of good health. However, a natural tan is not always desirable since it requires prolonged exposure to UV radiation, in particular to UV-A radiation which causes the tanning of the skin but, however, is liable to induce an adverse change therein, in particular in the case of sensitive skin or of skin which is continually exposed to solar radiation. It is thus desirable to find an alternative to a natural tan which is compatible with the requirements of such skin types.

Most of the cosmetic products intended for artificially tanning the skin are based on carbonyl derivatives which, by interacting with the amino acids in the skin, allow the formation of colored products.

To this end, it is known that dihydroxy-acetone, or DHA, is a particularly advantageous product which is commonly used in cosmetics as an agent for artificially tanning the skin; when applied to the skin, in particular to the face, it gives a tanning or bronzing effect which is similar in appearance to that which may result from prolonged exposure to sunlight (a natural tan) or under a UV lamp.

A drawback of DHA is the length of time the coloration takes to develop: specifically, several hours (3 to 5 hours in general) are required for the coloration to be revealed. There is thus an increasing demand for fast-acting self-tanning products which give a coloration closer to that of a natural tan.

Thus, efforts are continually being made to find novel compounds and novel compositions which can give the skin an artificial coloration close to that of a natural tan in a simple, effective, fast and risk-free manner.

*Sorghum* extracts have been known for a long time as food colorants. They give a reddish brown color and have in their composition flavonoids, anthocyanidins and tannins.

SUMMARY OF THE INVENTION

Now, after considerable research conducted in the field of artificial coloring of the skin, the applicant has discovered that particular emulsions containing at least one organomodified silicone and, as skin-coloring agent, at least one *sorghum* extract, in the absence of a flavylium salt which is unsubstituted in position 3 and which is substituted with at least one hydroxyl or alkoxy radical, not only make it possible to give the skin, immediately after applying the product to it, an artificial coloration close to that of a natural tan, but also have good stability and are cosmetically pleasant.

These discoveries form the basis of the present invention.

The subject of the present invention is therefore a cosmetic or dermatological emulsion, characterized in that it comprises:
(a) at least one aqueous phase;
(b) at least one fatty phase;
(c) at least one *sorghum* extract;
(d) at least one organomodified silicone; the said composition not containing a flavylium salt which is unsubstituted in position 3 and which is substituted with at least one hydroxyl or alkoxy radical.

For the purposes of the present invention and in the text which follows, the expression "cosmetic or dermatological emulsion" means any emulsion whose aqueous phase and fatty phase consist of substances that are cosmetically or dermatologically acceptable for topical application to the skin.

A subject of the present invention is also a process for giving the skin an artificial coloration close to that of a natural tan, characterized in that it consists in applying to the skin an effective amount of a cosmetic composition as defined above.

A subject of the present invention is also the use of the emulsion for the manufacture of cosmetic compositions for coloring the skin.

A subject of the present invention is also the use of at least one *sorghum* extract and of an organomodified silicone in a cosmetic composition not containing a flavylium salt which is unsubstituted in position 3 and which is substituted with at least one hydroxyl or alkoxy radical, with the aim of obtaining an artificial coloration of the skin close to that of a natural tan.

The compositions and uses in accordance with the invention make it possible to obtain an artificial coloration close to that of a natural tan in a short space of time. Thus, an immediate coloration is obtained, which allows the application to be visualized and consequently allows more uniform spreading of the composition on the skin and thus of the resulting coloration.

For the purposes of the present invention, the expression "composition intended for artificially coloring the skin" will be understood to mean a formulation with a particular affinity for the skin which allows it to give the skin a long-lasting coloration, which is non-covering (that is to say which does not have a tendency to opacify the skin) and which is not removed either with water or with a solvent, and which withstands both rubbing and washing with a solution containing surfactants. Such a long-lasting coloration is thus distinguished from the superficial and transient coloration provided, for example, by a make-up product.

In accordance with the generally accepted definition, the term "silicone" means any organosilicone polymer or oligomer of linear or cyclic, branched or crosslinked structure, of variable molecular weight, obtained by polymerization and/or polycondensation of suitably functionalized silanes, and consisting essentially of a repetition of main units in which the silicon atoms are linked together via oxygen atoms (siloxane bond=Si—O—Si=), optionally substituted hydrocarbon-based radicals being directly linked via a carbon atom to the said silicon atoms. The hydrocarbon-based radicals that are most common are alkyl radicals, especially $C_1$–$C_{10}$ alkyl radicals and in particular methyl radicals, fluoroalkyl radicals and aryl radicals and in particular phenyl radicals. Silicones are defined in greater detail in the book by Walter Noll "Chemistry and Technology of Silicones" (1968) Academie Press.

Other characteristics, aspects and advantages of the present invention will become apparent on reading the detailed description which follows.

DETAILED DESCRIPTION OF BEST MODE AND SPECIFIC/PREFERRED EMBODIMENTS OF THE INVENTION

The organomodified silicones which may be used in accordance with the invention are silicones as defined above and comprising in their structure one or more organofunctional groups attached via a hydrocarbon-based radical. The silicones which may be used in accordance with the invention may be in the form of oils, waxes, resins or gums. They may be water-soluble or water-insoluble.

Among the organomodified silicones which may be mentioned are polyorganosiloxanes comprising:

(1) oxyalkylenated (in particular oxyethylenated and/or oxypropylenated) groups such as those disclosed in EP-0, 796,615 and corresponding to the following formulae:

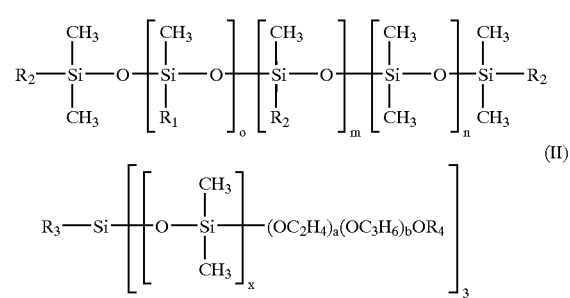

$R_1$, which may be identical or different, are each a linear or branched $C_1$–$C_{30}$ alkyl radical or a phenyl radical;

$R_2$, which may be identical or different, are each —$C_cH_{2c}$—(—O—$C_2H_4$)$_a$—(—O—$C_3H_6$)$_b$—(O—$C_4H_8$)$_d$—$R_5$;

$R_3$ and $R_4$, which may be identical or different, are each a linear or branched $C_1$–$C_{12}$ alkyl radical and preferably a methyl radical;

$R_5$, which may be identical or different, are each a hydrogen atom, a hydroxyl group, a linear or branched alkyl radical having 1 to 12 carbon atoms, a linear or branched alkoxy radical having 1 to 6 carbon atoms, a linear or branched acyloxy radical having 2 to 12 carbon atoms, —NHCH$_2$CH$_2$COOM, an aminoalkyl radical optionally substituted on the amine function, carboxy ($C_1$–$C_{30}$)acyl, an optionally substituted phosphono group, —O—CO—(CH$_2$)$_d$—CO$_2$M, —NHCO(CH$_2$)$_d$OH or —NH$_3$Y;

M, which may be identical or different, are each a hydrogen atom, Na, K, Li, NH$_4$ or an organic amine;

a ranges from 0 to 50;
b ranges from 0 to 50;
c ranges from 0 to 4;
a+b is greater than or equal to 1;
d ranges from 0 to 10;
m ranges from 0 to 20;

n ranges from 0 to 500;
p ranges from 0 to 20;
x ranges from 1 to 100; and
Y is a mineral or organic monovalent anion such as halide (chloride or bromide), sulphate or carboxylate (acetate, lactate or citrate); such as, for example, those sold under the trademarks Fluid DC 193 by Dow Corning, SILWET L 77 by OSI and MAZIL 756 by Mazer PPG; mention may also be made of the products sold under the names "Silicone DC 3225C" and "DC Q2-5200" by Dow Corning;

(2) alkoxy groups, such as the product sold under the name "Silicone Copolymer F-755" by SWS Silicones and ABIL Wax 2428, 2434 and 2440 by Goldschmidt;

(3) anionic groups such as 2-hydroxyalkylsulphonate; 2-hydroxyalkylthiosulphate, such as the products sold by Goldschmidt under the names "ABIL S201" and "ABIL 5255";

(4) thiol groups, such as the products sold under the names "GP 72 A" and "GP 71" by Genesee;

(5) anionic groups of the carboxylic type, such as the organomodified silicones disclosed in WO 95/23579, EP-A-0,219,830 and WO 98/20883 and in particular those corresponding to formula (III) below:

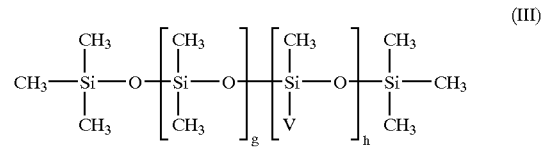

in which V is a radical —(R$^1$O)$_e$—R$^2$—(OR$^3$)$_i$—COOM, in which R$^1$ and R$^3$ independently are each a linear or branched alkylene radical having from 2 to 20 carbon atoms, R$^2$ is a linear or branched alkylene radical having from 1 to 50 carbon atoms which may comprise a hydroxyl group; e is 0 or i and f is a number ranging from 0 to 200; M is hydrogen, an alkali metal or alkaline earth metal, NH$_4$ or a quaternary ammonium group such as a mono-, di-, tri- or tetra($C_1$–$C_4$ alkyl)ammonium group; g and h are numbers ranging from 0 to 1,000, the sum c+d preferably ranging from 2 to 1,000; for example those sold under the trademark Huile M 642 by Wacker, under the names SLM 23 000/1 and SLM 23 000/2 by Wacker, under the name 176-12057 by General Electric, under the name FZ 3703 by OSI or under the name BY 16 880 by Toray Silicone; mention may also be made of the products disclosed in patent EP-186,507 from Chisso Corporation, or of the alkylcarboxylic type, such as those present in the product X-22-3701E from Shin-Etsu;

(6) hydroxylated groups, for instance the polyorganosiloxanes containing a hydroxyalkyl function disclosed in FR-A-8,516,334, corresponding to the formula (IV):

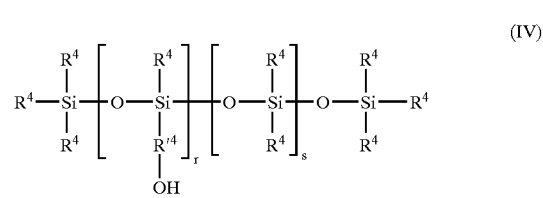

in which the radicals R$^4$, which may be identical or different, are each a methyl or phenyl radicals, at least 60 mol % of the radicals R$^4$ being methyl radicals; the radical R$^{'4}$ is a divalent hydrocarbon-based $C_2$–$C_{18}$ alkylene chain structural unit; r ranges from 1 to 30 inclusive; and s ranges from 1 to 150 inclusive;

(7) acyloxyalkyl groups such as, for example, the polyorganosiloxanes disclosed in FR-A-2,641,185 and corresponding to the formula (V):

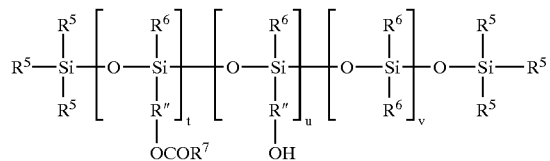

in which $R^5$ is a methyl, phenyl, —$OCR^7$ or hydroxyl group, only one of the radicals $R_4$ per silicon atom possibly being OH; $R^6$ is methyl or phenyl, at least 60 mol % of all of the radicals $R_4$ and $R'_4$ being methyl radicals; $R^7$ is a $C_8$–$C_{20}$ alkyl or alkenyl radical; R" is a linear or branched divalent hydrocarbon-based $C_2$–$C_{18}$ alkylene radical; t ranges from 1 to 120 inclusive; u ranges from 1 to 30; v is equal to 0 or is less than 0.5 t; and t+u ranges from 1 to 30; the polyorganosiloxanes of formula (V) may contain groups:

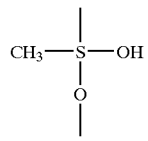

in proportions not exceeding 15% of the sum t+u+v;

(8) substituted or unsubstituted amine groups such as the silicones disclosed in EP-A-0,852,488 and in particular aminosilicones chosen from:
(a) the polysiloxanes corresponding to the formula:

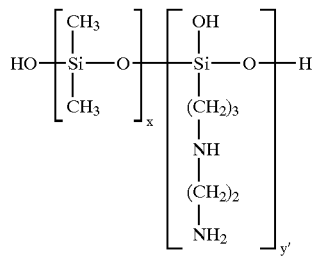

in which x' and y' are integers dependent on the molecular weight, generally such that the said number-average molecular weight ranges from 5,000 to 500,000;
(b) the cationic silicone polymers having the formula:

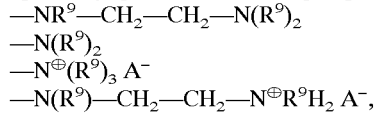

in which G is a hydrogen atom or a phenyl radical, OH or a $C_1$–$C_8$ alkyl group, for example methyl, i is the number 0 or an integer ranging from 1 to 3; j is 0 or 1 and in particular 1; k and l are numbers such that the sum (n+m) ranges from 1 to 2,000 and in particular from 50 to 150; n is a number ranging from 0 to 1,999 and especially from 49 to 149 and m is a number ranging from 1 to 2,000 and especially from 1 to 10; $R^8$ is a monovalent radical of formula —$C_qH_{2q}L$ in which q is a number ranging from 2 to 8 and L is an optionally quaternized amine group selected from among:
—$NR^9$—$CH_2$—$CH_2$—$N(R^9)_2$
—$N(R^9)_2$
—$N^\oplus(R^9)_3$ $A^-$
—$N(R^9)$—$CH_2$—$CH_2$—$N^\oplus R^9 H_2$ $A^-$, in which $R^9$ is hydrogen, phenyl, benzyl or a saturated monovalent hydrocarbon-based radical, for example an alkyl radical containing from 1 to 20 carbon atoms and $A^-$ is a halide ion such as, for example, fluoride, chloride, bromide or iodide;
(c) the cationic silicone polymers having the formula:

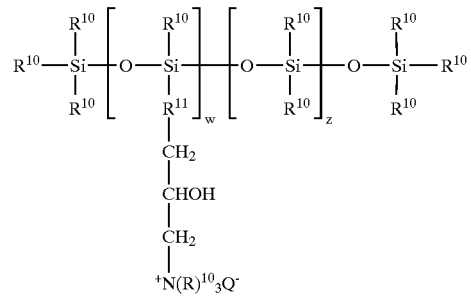

in which $R^{10}$ is a monovalent hydrocarbon-based radical having from 1 to 18 carbon atoms and in particular a $C_1$–$C_{18}$ alkyl or $C_2$–$C_{18}$ alkenyl radical, for example methyl; $R^{11}$ is a divalent hydrocarbon-based radical, in particular a $C_1$–$C_{18}$ alkylene radical or a divalent $C_1$–$C_{18}$, for example $C_1$–$C_8$, alkylenoxy radical; $Q^-$ is a halide ion, especially chloride; w represents an average statistical value from 2 to 20 and in particular from 2 to 8; and z represents an average statistical value from 20 to 200 and in particular 20 to 50; by way of example of aminosilicones, mention may be made of the products sold under the name GP 4 Silicone Fluid and GP 7100 by Genesee or the products sold under the names Q2 8220 and Dow Corning 929 or 939 by Dow Corning;

(9) hydroxyacylamino groups, for instance the polyorganosiloxanes disclosed in EP-342,834. Mention may be made, for example, of the product Q2-8413 from Dow Corning;

(10) groups of optionally substituted aryl type such as, for example, phenyl, naphthyl, benzyl or phenethyl, such as the non-volatile arylsilicones disclosed in EP-A-822,202; examples of these compounds which may be mentioned are those sold by Bayer under the name Huile BAYSILONE Fluid PD5, by Dow Corning under the name Dow Corning 556 Fluid, by Rhône-Poulenc under the names MIRASIL DPDM, RHODORSIL HUILE 510 V 100, RHODORSIL HUILE 550, RHODORSIL HUILE 510V500 and RHODORSIL HUILE 710, and under the names WACKER BELSIL PDM 20, PDM 200 and PDM 1000 by Wacker.

The organomodified silicone(s) according to the present invention is (are) preferably present in concentrations ranging from 0.1% to 40% relative to the total weight of the composition and more preferably in an amount ranging from 0.5% to 20%.

The compositions in accordance with the present invention make it possible to obtain, 30 minutes after application to a fair skin at a rate of 2 mg/cm², a darkening characterized in the (L*, a*, b*) calorimetric measuring system by a $\Delta L^*$ ranging from −0.5 to −20. Preferably, $\Delta L^*$ will range from −0.5 to −15.

The compositions in accordance with the present invention give, 30 minutes after application to a fair skin at a rate of 2 mg/cm$^2$, a coloration defined in the (L*, a*, b*) colorimetric measuring system by a ratio $\Delta a^*/\Delta b^*$ ranging from 0.5 to 3 and even more particularly ranging from 0.8 to 2.

According to the present invention, the term "fair skin" means an untanned skin whose calorimetric characteristics may be defined by its ITA angle as defined in the publication by A. Chardon et al. "Skin Color Typology and Suntanning Pathways" presented at the 16th IFSCC congress, Oct. 8–10, 1990, New York, and in *Int. J. Cosm. Sci.* 13 191–208 (1991). The fair skins as defined in this classification have an ITA angle of between 35 and 55. In the (L*, a*, b*) calorimetric measuring system:

L* represents the luminance or clarity, a* represents the red-green axis (−a*=green, +a*=red) and b* represents the yellow-blue axis (−b*=blue, +b*=yellow). Thus, a* and b* express the shade of the skin.

$\Delta L^*$ reflects the darkening of the color: the more negative the $\Delta L^*$, the darker the color, with:

ti $\Delta L^* = L^*$ uncolored skin−$L^*$ colored skin.

The ratio $\Delta a^*/\Delta b^*$ reflects the red/yellow balance and thus the shade, with:

$\Delta a^* = a^*$ uncolored skin−$a^*$ colored skin $\Delta b^* = b^*$ uncolored skin−$b^*$ colored skin.

The *sorghum* extracts in accordance with the invention are obtained from the whole plant, the stems, the seeds or the leaves of the genus *Sorghum*. The preferred species of *sorghum* are chosen from *Sorghum bicolor, Sorghum caudatum, Sorghum nervosum, Sorghum durra, Sorghum vulgare* and the *Sorghum* species in association with *Colletotrichum graminicola*.

The *sorghum* extracts in accordance with the invention are more particularly the extracts of *Sorghum vulgare* such as the commercial product *Sorghum* Extract Absorbance>30 sold by Premier Specialties.

The *sorghum* extracts in accordance with the invention are obtained from the extraction of the whole plant or of the plant parts cited above which may be in the fresh state or in the dry state.

The *sorghum* extract in accordance with the invention may be obtained by a process comprising the following steps:

(a) an extraction of the whole plant, the stems, the seeds or the leaves of *Sorghum* in an aqueous medium which may also contain at least one organic solvent;

(b) a maceration in an alkaline medium having a pH on the order of 11–12;

(c) optionally a precipitation from the maceration medium by addition of an acid so as to reach a pH on the order of 1–2.

The extraction may be carried out in an acidic medium as described in the Chinese patents CN 1035512 C and CN 1064284A and in the publication by M KOUDA-BONAFOS, E CZYZEWSKA, M NACRO and AC OEHLSCHLAGER. "Isolation of apigenin from leaf sheets of *Sorghum caudatum*" Journal of Chemical Ecology, Vol. 20, No. 8, p. 2123–2125 (1995).

The extraction may also be carried out in an alkaline medium followed by precipitation in an acidic medium as described in the Chinese patent CN 1065079A and in the publication by J P REY, J L POUSSET, J LEVESQUE and P WANTY. "Isolation and composition of a natural dye from the stems of *sorghum* bicolor (L.) Moench subsp. Americanum caudatum" Cereal Chem. Vol. 70(6), p. 759–25 760 (1993).

The extraction may also be carried out in an organic medium as described in the publications by J WANG "Studies on extraction of pigment from *sorghum* husks and its properties" Huaxue Shijie, Vol. 39 (4), p. 211–213 (1998) and by A SEREME, M KOUDA-BONAFOS and M NACRO "Phenolic compounds in *Sorghum caudatum* tissues during plant development" Biomass and Bioenergy Vol. 4(1), p. 69–71 (1993).

The organic solvents used for the extraction may be alcohols such as ethanol, methanol, normal primary propyl alcohol, isopropyl alcohol, normal primary butyl alcohol, propylene glycol and glycerol for example. The organic solvents may also be represented by diethyl ether, acetone, ethyl methyl ketone, ethyl acetate for example. The organic solvents used may also be supercritical fluids or fluorinated solvents such as dodecafluoropentane, tetradecafluorohexane, perfluorinated N-methylmorpholine and methoxynonafluorobutane for example.

Step (b) of maceration in an alkaline medium may be carried out for a period of 15–25 days at a temperature of 60–80° C. in a 0.1N sodium hydroxide solution having a pH on the order of 11–12.

Step (c) of precipitation by addition of acid may be carried out, for example, with 10N hydrochloric acid so as to reach a pH on the order of 1–2. The aqueous suspension thus obtained is then filtered in order to recover the precipitate which is then dried.

Steps (b) and (c) may be repeated several times.

The concentration of *sorghum* extract in accordance with the invention preferably varies from 0.0001% to 10%, and still more preferably from 0.001% to 5% by weight, relative to the total weight of the composition.

The compositions of the invention may be prepared according to the techniques that are well known to those skilled in the art, in particular those intended for preparing oil-in-water or water-in-oil emulsions.

These compositions may be in particular in the form of a simple or complex (O/W, W/O, O/W/O or W/O/W) emulsion such as a cream, a milk, a gel or a cream-gel, a powder or a solid tube and may optionally be packed as an aerosol and may be in the form of a mousse or a spray. The acronyms O/W, W/O, O/W/O and W/O/W stand for oil-in-water, water-in-oil, oil-in-water-in-oil and water-in-oil-in-water, respectively.

In a particularly preferred manner, the compositions according to the invention are in the form of water-in-silicone emulsions and the organomodified silicone used preferably comprises oxyalkylenated (in particular oxyethylenated and/or oxypropylenated) groups such as those of formula (I) or (II) defined above.

The compositions according to the invention may also contain agents for artificially tanning and/or bronzing the skin (self-tanning agents).

The mono- or polycarbonyl-containing self-tanning agents are chosen, for example, from isatin, alloxan, ninhydrin, glyceraldehyde, mesotartaric aldehyde, glutaraldehyde, erythrulose, pyrazoline-4,5-dione derivatives as described in FR-2,466,492 and WO 97/35842, dihydroxyacetone (DHA), 4,4-dihydroxypyrazoline-5-one derivatives as described in EP-903,342, it being possible for these self-tanning agents to be combined or otherwise with direct dyes or indole derivatives.

In a preferred embodiment of the invention, dihydroxyacetone (DHA) will be more particularly used.

The mono- or polycarbonyl-containing self-tanning agents are generally present in the compositions according to the invention in proportions ranging from 0.1% to 10% by weight relative to the total weight of the composition, and preferably from 0.2% to 8% by weight relative to the total weight of the composition.

According to a particular form, the compositions of the invention may additionally contain one or more ultraviolet radiation screening agents.

The ultraviolet radiation screening agents may be chosen from organic UV screening agents or inorganic UV radiation screening agents.

The organic UV screening agents in accordance with the invention may be water-soluble, fat-soluble or insoluble in the customary cosmetic solvents. They are chosen in particular from anthranilates; cinnamic derivatives; dibenzoylmethane derivatives; salicylic derivatives; camphor derivatives; triazine derivatives such as those disclosed in U.S. Pat. No. 4,367,390, EP-863,145, EP-517,104, EP-570,838, EP-796,851, EP-775,698, EP-878,469 and EP-933,376; benzophenone derivatives in particular those described in EP-A-1,046,391 and DE-10,012,408; benzalmalonate derivatives; β,β'-diphenylacrylate derivatives; benzotriazole derivatives; benzimidazole derivatives; imidazolines; bis-benzoazolyl derivatives such as those disclosed in EP-669,323 and U.S. Pat. No. 2,463,264; p-aminobenzoic acid (PABA) derivatives;

methylenebis(hydroxyphenylbenzotriazole) derivatives as disclosed in U.S. Pat. No. 5,237,071, 5,166,355, GB-2,303, 549, DE-19,726,184 and EP-893,119; screening polymers and screening silicones such as those disclosed in particular in WO 93/04665; dimers derived from α-alkylstyrene, such as those disclosed in DE-19,855,649; 4,4-diarylbutadiene derivatives such as those disclosed in EP-0,967,200, DE-19, 755,649, EP-1,333,981 and mixtures thereof.

As examples of organic screening agents, mention may be made of those indicated below under their INCI (International Nomenclature of Cosmetic Ingredients) name:

para-Aminobenzoic Acid Derivatives:
PABA,
Ethyl PABA,
Ethyl Dihydroxypropyl PABA,
Ethylhexyl Dimethyl PABA sold in particular under the name "ESCALOL 507" by ISP,
Glyceryl PABA,
PEG-25 PABA sold under the name "UVINUL P25" by BASF,
Salicylic Derivatives:
Homosalate sold under the name "EUSOLEX HMS" by RONA/EM Industries,
Ethylhexyl Salicylate sold under the name "NEO HELIOPAN OS" by Haarmann and Reimer,
Dipropyleneglycol Salicylate sold under the name "DIPSAL" by Scher,
TEA Salicylate, sold under the name NEO HELIOPAN TS by Haarmann and Reimer,
Dibenzoylmethane Derivatives:
Butyl Methoxydibenzoylmethane sold in particular under the trademark "PARSOL 1789" by Hoffmann La Roche,
Isopropyl Dibenzoylmethane,
Cinnamic Derivatives:
Ethylhexyl Methoxycinnamate sold in particular under the trademark "PARSOL MCX" by Hoffmann La Roche,
Isopropyl Methoxycinnamate,
Isoamyl Methoxycinnamate sold under the trademark "NEO HELIOPAN E 1000" by Haarmann and Reimer,
Cinoxate,
DEA Methoxycinnamate,
Diisopropyl Methylcinnamate,
Glyceryl Ethylhexanoate Dimethoxycinnamate
β,β'-Diphenylacrylate Derivatives:
Octocrylene sold in particular under the trademark "UVINUL N539" by BASF,
Etocrylene, sold in particular under the trademark "UVINUL N35" by BASF,
Benzophenone Derivatives:
Benzophenone-1 sold under the trademark "UVINUL 400" by BASF,
Benzophenone-2 sold under the trademark "UVINUL D50" by BASF,
Benzophenone-3 or Oxybenzone, sold under the trademark "UVINUL M40" by BASF,
Benzophenone-4 sold under the trademark "UVINUL MS40" by BASF,
Benzophenone-5,
Benzophenone-6 sold under the trademark "HELISORB 11" by Norquay,
Benzophenone-8 sold under the trademark "SPECTRA-20 SORB UV-24" by American Cyanamid,
Benzophenone-9 sold under the trademark "UVINUL DS-49" by BASF,
Benzophenone-12
Benzylidenecamphor Derivatives:
3-Benzylidenecamphor manufactured under the name "MEXORYL SD" by Chimex,
4-Methylbenzylidenecamphor sold under the name "EUSOLEX 6300" by Merck,
Benzylidenecamphor Sulfonic Acid manufactured under the name "MEXORYL SL" by Chimex,
Camphor Benzalkonium Methosulfate manufactured under the name "MEXORYL SO" by Chimex,
Terephthalylidene Dicamphor Sulfonic Acid manufactured under the name "MEXORYL SX" by Chimex,
Polyacrylamidomethyl Benzylidene Camphor manufactured under the name "MEXORYL SW" by Chimex,
Phenylbenzimidazole Derivatives:
Phenylbenzimidazole Sulfonic Acid sold in particular under the trademark "EUSOLEX 232" by Merck,
Benzimidazilate sold under the trademark "NEO HELIOPAN AP" by Haarmann and Reimer,
Triazine Derivatives:
Anisotriazine sold under the trademark "TINSORB S" by Ciba Geigy,
Ethylhexyl Triazone sold in particular under the trademark "UVINUL T150" by BASF,
Diethylhexyl Butamido Triazone sold under the trademark "UVASORB HEB" by Sigma 3V,
2,4,6-Tris(diisobutyl 4'-aminobenzalmalonate)-s-triazine,
Phenylbenzotriazole Derivatives:
Drometrizole Trisiloxane sold under the name "Silatrizole" by Rhodia Chimie,
Methylene bis-Benzotriazolyl Tetramethylbutylphenol, sold in solid form under the trademark "MIXXIM.24 BB/100" by Fairmount Chemical or in micronized form as an aqueous dispersion under the trademark "TINOSORB M" by Ciba Specialty Chemicals, Anthranilic Derivatives:
Menthyl anthranilate sold under the trademark "NEO HELIOPAN MA" by Haarmann and Reimer,
Imidazoline Derivatives:
Ethylhexyl Dimethoxybenzylidene Dioxoimidazoline Propionate,
Benzalmalonate Derivatives:
Polyorganosiloxane containing benzalmalonate functional groups sold under the trademark "PARSOL SLX" by Hoffmann La Roche
4,4-Diarylbutadiene Derivatives:
1,1-Dicarboxy(2,2'-dimethylpropyl)-4,4-diphenyl-butadiene and mixtures thereof.

The organic UV screening agents most particularly preferred are chosen from the following compounds:
Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic,
Benzophenone-3,
Benzophenone-4,
Benzophenone-5,
4-Methylbenzylidene Camphor,
Benzimidazilate,
Anisotriazine,
Ethylhexyl Triazone,
Diethylhexyl Butamide Triazone,
Methylene bis-Benzotriazolyl Tetramethylbutylphenol, 1,1-Dicarboxy(2,2'-dimethyl-propyl)-4,4-diphenyl-butadiene Drometrizole Trisiloxane, and mixtures thereof.

The inorganic screening agents are generally pigments or alternatively nanopigments (average size of the primary particles: generally between 5 nm and 100 nm and preferably between 10 nm and 50 nm) of metal oxides which are coated or uncoated, such as, for example, nanopigments of titanium oxide (amorphous or crystallized in rutile and/or anatase form), of iron oxide, of zinc oxide, of zirconium oxide or of cerium oxide, which are all UV stabilizers that are well known per se. Conventional coating agents are, moreover, alumina and/or aluminium stearate. Such coated or uncoated metal oxide nanopigments are disclosed in particular in EP-A-0,518,772 and EP-A-0,518,773.

The radiation screening agents in accordance with the invention are generally present in the compositions according to the invention in proportions ranging from 0.1% to to 20% by weight relative to the total weight of the composition, and preferably ranging from 0.2% to 15% by weight relative to the total weight of the composition.

The compositions of the invention may also comprise conventional cosmetic adjuvants chosen in particular from fatty substances, organic solvents, thickeners, softeners, opacifiers, stabilizers, emollients, antifoams, moisturizers, fragrances, preserving agents, polymers, fillers, sequestering agents, propellants, acidifying or basifying agents or any other ingredient usually used in cosmetics, in particular for manufacturing antisun compositions in the form of emulsions.

The fatty substances may consist of an oil or a wax or mixtures thereof, and they also comprise fatty acids, fatty alcohols and fatty acid esters. The oils may be chosen from animal, plant, mineral and synthetic oils and especially from liquid paraffin, volatile or non-volatile silicone oils, isoparaffins, polyolefins, fluoro oils and perfluoro oils. Similarly, the waxes may be chosen from the animal, fossil, plant, mineral and synthetic waxes that are known per se.

Among the organic solvents, mention may be made of lower alcohols and polyols. The latter may be chosen from glycols and glycol ethers such as ethylene glycol, propylene glycol butylene glycol, dipropylene glycol or diethylene glycol.

Needless to say, a person skilled in the art will take care to select this/these optional additional compound(s) and/or the amounts thereof such that the advantageous properties, in particular the water resistance and stability, intrinsically associated with the emulsions in accordance with the invention are not, or are not substantially, adversely affected by the addition(s) envisaged.

When it is an emulsion, the aqueous phase of this emulsion may comprise a nonionic vesicular dispersion prepared according to known processes (Bangham, Standish and Watkins, J. Mol. Biol. 13, 238 (1965), FR-2,315,991 and FR-2,416,008).

When the cosmetic composition according to the invention is used for coloring the human epidermis, it may be in the form of a suspension or a dispersion in solvents or fatty substances, in the form of a nonionic vesicular dispersion or in the form of an emulsion, preferably an oil-in-water emulsion, such as a cream or a milk, in the form of an ointment, a gel, a cream-gel, a solid tube, a powder, a stick, an aerosol mousse or a spray.

As indicated at the start of the description, another subject of the present invention is the use of an emulsion according to the invention to manufacture cosmetic compositions for coloring the skin and/or the hair.

Concrete but in no way limiting examples illustrating the invention will now be given.

EXAMPLE 1

This example is intended to show, firstly, the resistance to washing of a composition A according to the invention containing the extract of *sorghum* in an emulsion (water-in-silicone) support containing an organomodified silicone, compared with a composition B containing the extract of *sorghum* in an emulsion (oil-in-water) support not containing organomodified silicone.

This example is intended to show, secondly, that composition A in accordance with the present invention, applied to fair skin, rapidly gives a coloration close to that of a natural tan, in contrast with an emulsion C of the prior art containing an organomodified silicone but containing DHA instead of the extract of *sorghum*.

The Applicant prepared the following compositions:
Composition A (Invention):

| | |
|---|---|
| Polydimethyl/methyl siloxane POE/POP (396/4)(EO/PO 18/18) A 10% D5 | 10 g |
| Cyclopentadimethylsiloxane | 12.5 g |
| Mixture or natural tocopherols/soybean oil | 0.1 g |
| Propylene glycol | 15 g |
| Extract of Sorghum vulgare (Sorghum Extract Absorbance > 30 from Premier Specialties) | 0.7 g |
| Preservatives    qs | |
| Demineralized water    qs | 100 g |

Composition B (Not According to the Invention):

| | |
|---|---|
| Mixture of glyceryl mono-distearate/ oxyethylenated cetylstearyl alcohol | 3 g |

-continued

| | |
|---|---|
| Stearyl alcohol | 2.5 g |
| Mixture of glyceryl mono-distearate/ polyethylene glycol stearate | 2.5 g |
| Polydimethylsiloxane | 1 g |
| Extract of Sorghum vulgare (Sorghum Extract Absorbance > 30 from Premier Specialties) | 0.7 g |
| Propylene glycol | 15 g |
| Preservatives qs | |
| Demineralized water qs | 100 g |

Protocol for Evaluation:

Compositions A and B were applied at the rate of 2 mg/cm² to an area of 2×2 cm² delimited on the back of the forearm of which the skin color, characterized by the ITA angle, is between 35 and 55.

The following series of colorimetric measurements were taken using a MINOLTA CM-508d spectrocolorimeter:
1) before applying the composition,
2) 30 minutes after the application,
3) 30 minutes after application and washing of the areas with cotton wool impregnated with dilute shower gel (shower gel Neutralia at 2%).

The results are expressed in the (L*, a*, b*) system in which L* represents the luminance, a* represents the red-green axis (−a*=green, +a*=red) and b* represents the yellow-blue axis (−b*=blue, +b*=yellow). Thus, a* and b* express the shade of the skin.

To evaluate the intensity of the coloration, the important value is the ΔL* which reflects the darkening of the color: the more negative the ΔL*, the darker the color, with:

$\Delta L^* = L^*$ uncolored skin $- L^*$ colored skin.

For the shade of the coloration obtained, the important value is the ratio Δa*/Δb* which reflects the red/yellow balance and thus the shade, with:

$\Delta a^* = a^*$ uncolored skin $- a^*$ colored skin $\Delta b^* = b^*$ uncolored skin $- b^*$ colored skin.

The results obtained are collated in Table (I) below:

TABLE I

| | Composition A (invention) ΔL* | Composition B (not according to the invention) ΔL* |
|---|---|---|
| T = 30 minutes | −5 | −6.2 |
| T = 30 minutes after washing with water | −3.9 | −1.72 |
| % loss of ΔL | 22% | 73% |

It is thus found that composition A, which contains the *sorghum* extract as coloring agent, makes it possible to obtain better resistance to washing (% loss of ΔL=22%) than composition B which contains the same coloring agent at the same concentration (% loss of ΔL=73%).

Comparison with an Emulsion Containing DHA:

The Applicant Prepared the Following Composition:

Composition C (Not According to the Invention):

| | |
|---|---|
| Polydimethyl/methyl siloxane POE/POP (396/4)(EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Polypropylene glycol | 15 g |
| Preservatives qs | |
| Demineralized water qs | 100 g |

Compositions A and C were applied at a rate of 2 mg/cm² to an area of 2×2 cm² delimited on the back of the forearm skin color of which, characterized by the ITA angle, is between 35 and 55.

The following series of colorimetric measurements were taken using a MINOLTA CM-508d colorimeter:
1) before applying the composition,
2) 30 minutes after application.

The results are expressed in the (L*, a*, b*) system in which L* represents the luminance, a* represents the red-green axis (−a*=green, +a*=red) and b* represents the yellow-blue axis (−b*=blue, +b*=yellow). Thus, a* and b* express the shade of the skin.

To evaluate the intensity of the coloration, the important value is the ΔL* which reflects the darkening of the color: the more negative the ΔL*, the darker the color, with:

$L^* = L^*$ uncolored skin $- L^*$ colored skin.

The results obtained are collated in Table (II) below:

TABLE II

| | Composition A (invention) ΔL* | Composition B (not according to the invention) ΔL* |
|---|---|---|
| T = 30 minutes | −5 | −0.4 |

It is thus found that 30 minutes after application, composition C, which contains DHA as skin-coloring agent, gives the skin only a very faint coloration, since the DHA has not yet had time to act (ΔL*=−0.4). On the other hand, composition A according to the invention has already given the skin a significant coloration (ΔL*=−5).

Composition C containing DHA does not give after 30 minutes a darkening comparable to that of composition A.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological artificial tanning emulsion, comprising (a) at least one aqueous phase and (b) at least one fatty phase, (c) an effective artificial tanning amount of at least one *sorghum* extract, and (d) at least one organomodified silicone, said emulsion being devoid of any flavylium salt that is unsubstituted at position 3 thereof, but which is otherwise substituted with at least one hydroxyl group or alkoxy radical.

2. The cosmetic/dermatological artifical tanning emulsion as defined by claim 1, further comprising at least one UV radiation screening agent.

3. The cosmetic/dermatological artifical tanning emulsion as defined by claim 2, said at least one UV radiation screening agent comprising an organic UV screening agent or an inorganic UV radiation screening agent.

4. The cosmetic/dermatological artifical tanning emulsion as defined by claim 3, comprising at least one organic UV screening agent that is water-soluble, fat-soluble or insoluble in a usual cosmetic solvent.

5. The cosmetic/dermatological artifical tanning emulsion as defined by claim 4, said at least one organic UV screening agent being selected from the group consisting of an anthranilate; a cinnamic derivative; a dibenzoylmethane derivative; a salicylic derivative; a camphor derivative; a triazine derivative; a benzophenone derivative, a β,β'-diphenylacrylate derivative; a benzotriazole derivative; a benzimidazole derivative; an imidazoline; a bis-benzoazolyl derivative; a p-aminobenzoic acid (PABA) derivative; a methylenebis(hydroxyphenylbenzotriazole) derivative; a screening polymer and a screening silicone; a dimer derived from α-alkylstyrene; and a 4,4-diarylbutadiene derivative, and mixtures thereof.

6. The cosmetic/dermatological artifical tanning emulsion as defined by claim 5, said at least one organic UV radiation screening agent being selected from the group consisting of:
Ethylhexyl Salicylate,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic Acid,
Benzophenone-3,
Benzophenone-4,
Benzophenone-5,
4-Methylbenzylidene Camphor,
Benzimidazilate,
Anisotriazine,
Ethylhexyl Triazone,
Diethylhexyl Butamido Triazone,
2,4,6-Tris(diisobutyl-4'-amionbenzalmalonate)-s-trazine,
Methylenebis-Benzotriazolyl Tetramethylbutylphenol,
Drometrizole Trisiloxane, and
1,1-Dicarboxy(2,2'-dimethyl-propyl)-4,4-diphenylbutadiene, and mixtures thereof.

7. The cosmetic/dermatological artifical tanning emulsion as defined by claim 3, comprsing at least one inorganic UV radiation screening agent selected from the group consisting of pigments and nanopigments of metal oxides which are coated and noncoated.

8. The cosmetic/dermatological artifical tanning emulsion as defined by claim 7, said at least one inorganic UV radiation screening agent comprising nanopigments of titanium, iron, zinc, zirconium or cerium oxide, which are coated or uncoated.

9. The cosmetic/dermatological artifical tanning emulsion as defined by claim 2, in which said at least one UV radiation screening agent is present in a proportion ranging from 0.1% to 15% by weight relative to the total weight thereof.

10. The cosmetic/dermatological artifical tanning emulsion as defined by claim 1, further comprising at least one mono- or polycarbonyl-containing atrificial/self-tanning agent.

11. The cosmetic/dermatological artifical tanning emulsion as defined by claim 10, said at least one polycarbonyl-containing artificial/self-tanning agent being selected from the group consisting of isatin, alloxan, ninhydrin, glyceraldehyde, mesotartaric aldehyde, glutaraldehyde, erythrulose, a pyrazoline-4,5-dione derivative, dihydroxyacetone (DHA), and a 4,4-dihydroxypyrazoline-5-one derivative, optionally combined with a direct dye or an indole derivative.

12. The cosmetic/dermatological artifical tanning emulsion as defined by claim 11, said at least one artificial/self-tanning agent comprising dihydroxyacetone (DHA).

13. The cosmetic/dermatological artifical tanning emulsion as defined by claim 10, in which the at least one artificial/self-tanning agent is present in a proportion ranging from 0.1% to 10% by weight relative to the total weight thereof.

14. The cosmetic/dermatological artifical tanning emulsion as defined by claim 1, said at least one organomodified silicone being selected from the group consisting of:
(1) polyorganosiloxanes comprising oxyalkylenated groups;
(2) polyorganosiloxanes comprising alkoxylated groups;
(3) polyorganosiloxanes comprising anionic functional groups;
(4) polyorganosiloxanes comprising thiol groups;
(5) polyorganosiloxanes comprising anionic carboxylic groups;
(6) polyorganosiloxanes comprising hydroxylated groups;
(7) polyorganosiloxanes comprising acyloxyalkyl groups;
(8) polyorganosiloxanes comprising substituted or unsubstituted amine groups;
(9) polyorganosiloxanes comprising hydroxyacylamino groups; and
(10) polyorganosiloxanes comprising optionally substituted aryl groups.

15. The cosmetic/dermatological artifical tanning emulsion as defined by claim 14, comprising polyorganosiloxanes bearing oxyalkylenated substituents and having one of the following formulae:

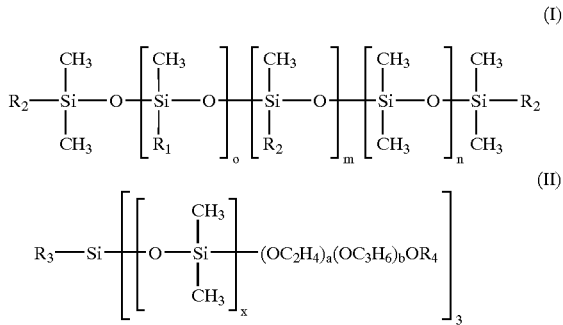

in which the radicals $R_1$, which may be identical or different, are each a linear or branched $C_1$–$C_{30}$ alkyl radical or a phenyl radical; the radicals $R_2$, which may be identical or different, are each —$C_cH_{2c}$—(—O—$C_2H_4$)$_a$—(—O—$C_3H_6$,$_b$—(O—$C_4H_8$)$_d$—$R_5$; the radicals $R_3$ and $R_4$, which may be identical or different, are each linear or branched $C_1$–$C_{12}$ alkyl radical; the radicals $R_5$, which may be identical or different, are each a hydrogen atom, a hydroxyl group, a linear or branched alkyl radical having 1 to 12 carbon atoms, a linear or branched alkoxy radical having 1 to 6 carbon atoms, a linear or branched acyloxy radical having 2 to 12 carbon atoms, —NHCH$_2$CH$_2$COOM, an aminoalkyl radical optionally substituted on the amine function, carboxy ($C_1$–$C_{30}$)acyl, an optionally substituted phosphono group, —O—CO—(CH$_2$)$_d$—CO$_2$M, —NHCO(CH$_2$)$_d$OH or —NH$_3$Y; the substituents M, which may be identical or different, are each a hydrogen atom, Na, K, Li, NH$_4$ or an organic amine; a ranges from 0 to 50; b ranges from 0 to 50; c ranges from 0 to 4; a+b is greater than or equal to 1; d ranges from 0 to 10; m ranges from 0 to 20; n ranges from 0 to 500; p ranges from 0 to 20; x ranges from 1 to 100; and Y is a mineral or organic monovalent anion.

16. The cosmetic/dermatological artifical tanning emulsion as defined by claim 14, comprising polyorganosiloxanes bearing anionic carboxylic group substituents and having the formula (III) below:

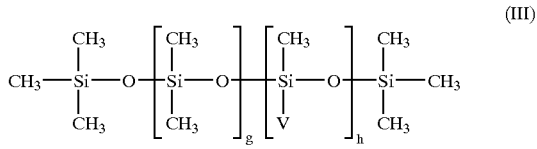
(III)

in which V is a radical —(R¹O)$_e$—R²—(OR³)$_f$—COOM, wherein $R^1$ and $R^3$ independently are each a linear of branched alkylene radical having from 2 to 20 carbon atoms; $R^2$ is a linear or branched alkylene radical having from 1 to 50 carbon atoms which may comprise a hydroxyl group; e is 0 or 1 and f is a number ranging from 0 to 200; M is hydrogen, an alkali metal or alkaline earth metal, $NH_4$ or a quaternary ammonium group; g and h are numbers ranging from 0 to 1,000; and the sum c+d ranging from 2 to 1,000.

17. The cosmetic/dermatological artifical tanning emulsion as defined by claim 14, comprising polyorganosiloxanes bearing hydroxylated substituents and having the formula (IV) below:

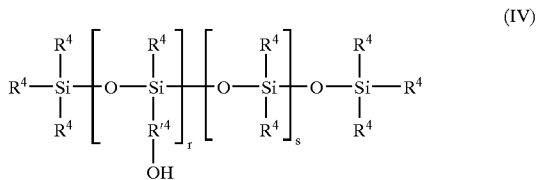
(IV)

in which the radicals $R^4$, which may be indentical or different, are each a methyl or phenyl radical, at least 60 mol % of the radicals $R^4$ being methyl radicals; the radical $R'^4$ is a divalent hydrocarbon-based $C_2$–$C_{18}$ alkylene chain structural unit; r ranges from 1 to 30 inclusive; and s ranges from 1 to 150 inclusive.

18. The cosmetic/dermatological artifical tanning emulsion as defined by claim 14, comprising polyorganosiloxanes bearing acyloxyalkyl substituents and having the formula (V):

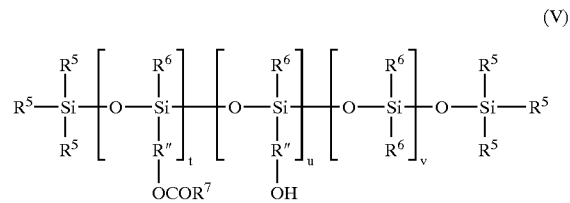
(V)

in which $R^5$ is methyl, phenyl, —OCOR⁷ or hydroxyl group, only one of the radicals $R_4$ per silicon atom being OH; $R^6$ is methyl or phenyl, at least 60 mol % of all of the radicals $R_4$ and $R'_4$ being methyl radicals; $R^7$ is a $C_8$–$C_{20}$ alkyl or alkenyl radical; R" is a linear or branched divalent hydrocarbon-based $C_2$–$C_{18}$ alkylene radical; t ranges from 1 to 120 inclusive; u ranges from 1 to 30; v is equal to 0 or is less than 0.5 t; and t+u ranges from 1 to 30; with the proviso that the polyorgansiloxanes of formula (V) may contain functional groups:

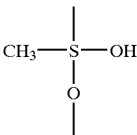

in proportions not exceeding 15% of the sum t+u+v.

19. The cosmetic/dermatological artifical tanning emulsion as defined by claim 14, comprising polyorganosiloxanes bearing substituted or unsubstituted amine substituents and selected from among:
(a) polysiloxanes having the formula:

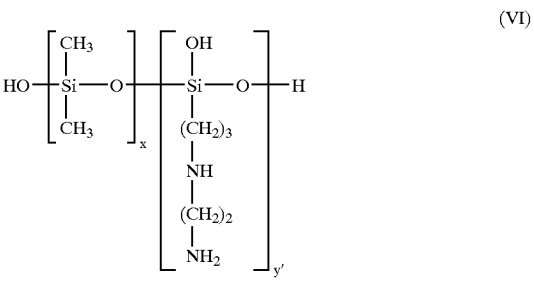
(VI)

in which x' and y' are integers such that the number average molecular weight thereof ranges from 5,000 to 500,000;
(b) cationic silicone polymers having the formula:

$$R^8{}_iG_{3-i}\text{-Si}(OSiG_2)_k\text{—}(OSiG_jR^8{}_{2-j})_l\text{—}O\text{—}SiG_{3-i}\text{-}R^8{}_i \quad \text{(VII)}$$

in which G is a hydrogen atom or a phenyl radical, OH or a $C_1$–$C_8$ alkyl radical; i is the number 0 or an integer from 1 to 3; j is 0 or 1; k and l are numbers such that the sum (n+m) ranges from 1 to 2,000; n is a number ranging from 0 to 1,999 and m is a number ranging from 1 to 2,000; $R^8$ is a monovalent radical of formula —$C_qH_{2q}L$ in which q is a number ranging from 2 to 8 and L is an optionally quaternized amine group selected from among:
—NR⁹—CH₂CH₂—N(R⁹)₂
—N(R⁹)₂
—N⊕(R⁹)₃A⁻
—N(R⁹)—CH₂—CH₂—N⊕R⁹H₂A⁻,
in which $R^9$ is hydrogen, phenyl, benzyl or a saturated monovalent hydrocarbon-based radical, and A⁻ is a halide ion;
(c) cationic silicone polymers having the formula:

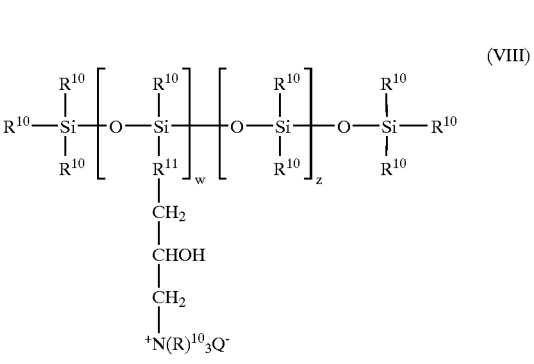
(VIII)

in which $R^{10}$ is a monovalent hydrocarbon-based radical having from 1 to 18 carbon atoms; $R^{11}$ is a divalent hydrocarbon-based radical; Q⁻ is a halide ion; w represents an average statistical value from 2 to 20; and z represents an average statistical value from 20 to 200.

20. The cosmetic/dermatological artifical tanning emulsion as defined by claim 1, said at least one *sorghum* extract being obtained from the whole plant, the stems, the seeds or the leaves of the genus *Sorghum*, in the fresh or dry state.

21. The cosmetic/dermatological artifical tanning emulsion as defined by claim 20, the species of *Sorghum* being selected from the group consisting of *Sorghum bicolor, Sorghum caudatum, Sorghum nervosum, Sorghum durra, Sorghum vulgare* and the *Sorghum* species in association with *Colletotrichum graminicola*.

22. The cosmetic/dermatological artifical tanning emulsion as defined by claim 20, said at least one *sorghum* extract being obtained from the whole plant, the stems, the seeds or the leaves of *Sorghum vulgare*.

23. The cosmetic/dermatological artifical tanning emulsion as defined by claim 1, comprising an amount of said at least one *sorghum* extract which is effective for obtaining, 30 minutes after application to a fair skin at a rate of 2 mg/cm$^2$, a coloration defined in the (L*,a*,b*) colorimetric measuring system by a ratio $\Delta a^*/\Delta b^*$ ranging from 0.5 to 3.

24. The cosmetic/dermatological artifical tanning emulsion as defined by claim 23, said ratio $\Delta a^*/\Delta b^*$ ranging from 0.8 to 2.

25. The cosmetic/dermatological artifical tanning emulsion as defined by claim 1, in which the at least one organomodified silicone is present in a concentration ranging from 0.1% to 40% relative to the total weight thereof.

26. The cosmetic/dermatological artifical tanning emulsion as defined by claim 1, comprising a water-in-silicone emulsion.

27. The cosmetic/dermatological artifical tanning emulsion as defined by claim 26, comprising an organomodified silicone bearing oxyalkylenated substituents.

28. The cosmetic/dermatological artifical tanning emulsion as defined by claim 1, comprising an amount of said at least one *sorghum* extract which is effective for obtaining, 30 minutes after application to a fair skin at a rate of 2 mg/cm$^2$, a darkening defined in the (L*,a*,b*) colorimetric measuring system by a $\Delta L^*$ ranging from −0.5 to −20.

29. The cosmetic/dermatological artifical tanning emulsion as defined by claim 28, said $\Delta L^*$ ranging from −0.5 to −15.

30. The cosmetic/dermatological artifical tanning emulsion as defined by claim 1, said at least one *sorghum* extract being obtained by a process comprising:
   (a) an extraction of parts from the whole plant, the stems, the seeds or the leaves of *Sorghum* in an aqueous medium which may also contain at least one organic solvent;
   (b) a maceration in an alkaline medium having a pH on the order of 11–12;
   (c) optionally, a precipitation from the maceration medium by addition of an acid to attain a pH on the order of 1–2.

31. The cosmetic/dermatological artifical tanning emulsion as defined by claim 1, in which the concentration of *sorghum* extract ranges from 0.0001% to 10% by weight, relative to the total weight thereof.

32. A regime or regimen for the artificial tanning of human skin, comprising topically applying thereon a thus effective amount of the cosmetic/dermatological artificial tanning emulsion as defined by claim 1.

* * * * *